United States Patent
Sandhaus

[11] Patent Number: 6,030,211
[45] Date of Patent: Feb. 29, 2000

[54] GUIDE APPARATUS FOR INSTRUMENTS, IN PARTICULAR FOR ORTHODONTAL AND DENTAL INSTRUMENTS

[76] Inventor: Sami Sandhaus, CH. DE l'Ormet 52, 1024 Ecublens, Switzerland

[21] Appl. No.: 09/046,924

[22] Filed: Mar. 24, 1998

[30] Foreign Application Priority Data

Jul. 21, 1997 [DE] Germany .......................... 197 31 194

[51] Int. Cl.$^7$ .................................................. A61C 3/02
[52] U.S. Cl. .............................................. 433/76; 433/109
[58] Field of Search ................... 433/50, 51, 75, 433/76, 109

[56] References Cited

U.S. PATENT DOCUMENTS

| | | | |
|---|---|---|---|
| 733,321 | 7/1903 | Griswold | 433/50 |
| 2,299,151 | 10/1942 | Kestler | 433/76 |
| 2,376,384 | 5/1945 | Ringle et al. | 433/50 |
| 3,083,462 | 4/1963 | Jermyn | 433/109 |
| 3,375,584 | 4/1968 | Cowan | 433/51 |
| 4,264,308 | 4/1981 | Tanaka | 433/75 |
| 4,344,755 | 8/1982 | Gold et al. | 433/76 |
| 5,163,842 | 11/1992 | Nonomura | 433/76 |
| 5,230,623 | 7/1993 | Guthrie et al. | 433/75 |
| 5,281,136 | 1/1994 | Giannella et al. | 433/76 |
| 5,332,391 | 7/1994 | Jermyn | 433/76 |
| 5,343,391 | 8/1994 | Mushabac | 433/76 |

FOREIGN PATENT DOCUMENTS

| | | | |
|---|---|---|---|
| 3 202 057 | 9/1982 | Germany | 433/109 |
| 3 339 656 | 5/1985 | Germany | 433/50 |
| 600844 | 9/1959 | Italy | 433/76 |

*Primary Examiner*—Ralph A. Lewis
*Attorney, Agent, or Firm*—Bachman & LaPointe, P.C.

[57] ABSTRACT

A guide apparatus for orthodontal and dental instruments used in producing cavities in bone tissue includes and instrument holder for receiving the orthodontal and dental instruments in a guide apparatus which is displaceable in three co-ordinate directions (x, y, z) and rotatable about at least one pivot axis (A).

13 Claims, 3 Drawing Sheets

GUIDE APPARATUS FOR INSTRUMENTS, IN PARTICULAR FOR ORTHODONTAL AND DENTAL INSTRUMENTS

BACKGROUND OF THE INVENTION

The invention concerns a guide apparatus for instruments, in particular orthodontal and dental instruments for producing cavities such as recesses and bores—for implants in bone tissue.

Bores and recesses—in particular slots—which are to be produced by drilling or milling are required for fitting implants in surgery, orthopedics or jaw and oral surgery. In most cases such bores and recesses are produced by a procedure whereby a drilling template is fitted on to the location to be provided with the cavity, the template acting as a guide means to permit the drilling operation to be effected with a relatively high degree of accuracy. The production of a slot is substantially more difficult as the transverse movement of the drill or milling tool has to be implemented by hand and this therefore presupposes a considerable degree of skill on the part of the operator. Abutments which are mounted to the drilling machine or to the drilling head are used to maintain the precise depth for such slots.

In all operations in which bores or slots have to be operatively produced in bone tissue, the influence of the operator skill remains a high-risk factor involved in such procedures, even when the abovementioned drilling templates which in most cases are produced on the basis of X-ray images help to improve the level of accuracy.

In regard to all known apparatuses and templates in the area of operational technology, there is no possibility of producing bores or slots with a high degree of precision by an automatic or semi-automatic procedure. Not least for that reason very long operating times have to be accepted and high levels of cost tolerated.

Accordingly, it is a principle object of the invention to provide a guide apparatus of the kind set forth above, which permits precise production of the cavities—in particular slots—, which shortens operating times and which reduces costs.

The foregoing object is achieved by way of the present invention wherein a guide apparatus for instruments, in particular for orthodontal and dental instruments for producing cavities such as recesses and bores for implants in bone tissue, characterised in that an instrument holder which receives the instrument is arranged at the guide apparatus which can be fixed at a fixed point, the instrument holder being displaceable in at least two mutually crossing directions and being rotatable about at least one pivot axis.

In accordance with the invention an instrument holder which receives the instrument is arranged at a guide apparatus—which can be fixed at a fixed point—displaceably in at least two mutually crossing directions and rotatably about at least one pivot axis. In that respect, it has been found advantageous if the instrument holder is mounted displaceably in three co-ordinate directions and/or rotatably about the pivot axis through an angle of more than 90°—preferably 360°. It is particularly advantageous for the instrument holder also to be arranged pivotably about a second pivot axis which crosses the first pivot axis.

The features according to the invention therefore provide a guide apparatus having an instrument holder for the drilling and milling head, which is to be set in linearly accurately fashion in more than two axes and which is also rotatable and inclinable with a high degree of precision.

In accordance with a further feature of the invention the instrument holder which is mounted to a working head of the guide apparatus is adapted to be displaceable transversely with respect to the longitudinal axis of the guide apparatus on a carriage or slider and is adapted to be lifted with the carriage or slider. It is preferably disposed laterally of the working head on a bar or the like strip of material which projects beyond same.

In accordance with the invention, a respective rotary handle for linear displacement by hand is provided for the path of movement of the instrument holder, which crosses the longitudinal axis, and for the stroke movement of the working head; each of the rotary handles may be replaced by an electrical, pneumatic or hydraulic drive.

It has also proven to be desirable for the working head to be rotatably connected by a pivot pin to a carrier tongue of an intermediate portion of the guide apparatus, which portion at the other end displaceably mounts to a carriage or slider connected to the fixed point. By virtue of the carriage or slider the intermediate portion with the working head is reversible parallel to the longitudinal axis of the guide apparatus.

At a spacing relative to that pivot pin the carrier tongue can be fixed to the intermediate portion rotatably about the longitudinal axis—that is to say at a right angle to the axis of the pivot pin. For that purpose the carrier tongue projects from a rotary disk which is connected to a shaft and which bears rotatably against a disk-like bearing surface of the intermediate portion. The rotary disk which is preferably rotatable through an angle of 360° is connected by way of the shaft to a setting knob by which it can be fixed in a desired rotational position.

Both the front carriage or slider on the working head, which is to be displaced transversely with respect to the longitudinal axis and which can also be lifted, and also the rear carriage or slider which in accordance with the invention is connected to the intermediate portion by way of an adjusting spindle and whose path of movement extends parallel to the longitudinal axis of the guide apparatus are each provided with a rotary handle for actuation thereof. If there is a wish to change over from manual operation to automatic operation, those rotary handles in accordance with the invention are themselves in the form of motors or drive means or are replaced by such.

Thus it is in accordance with the invention that the working head is designed to be displaceable in a plurality of axes by the carriages or sliders having a fine screwthread, with electrical, electronic, pneumatic or hydraulic drives. In that respect, on the one hand electrical stepping motors or electronic magnetic or dc motors are preferred as drives. On the other hand pneumatic drives are to be operated in particular with compressed air or compressed nitrogen as the drive medium; water or oil are preferred as the drive medium for hydraulic drives; in accordance with a further feature of the invention, they are to be passed in a closed circuit.

In accordance with the invention, preferably at least one display device for the setting data is associated with the actuating member or members or rotary handle or handles for the carriage or carriages and/or the rotary axis, for precise monitoring of the movements involved.

In accordance with further features of the invention, measurement scales can be provided on the carriage or carriages or the rotary axis or axes, and at least one electromechanical read-off system is possibly associated with the measurement scales.

It can also be of importance in regard to the invention that the entire installation as described can be set and adjusted by way of a computer, preferably by way of an X-ray picture which is fed into the computer; by virtue of the X-ray picture the installation can even be automatically set and adjusted.

If it is assumed that any drilling or milling unit which can be used in surgery or jaw or oral surgery can be mounted on the motion unit or the working head which is controlled in a plurality of axes, the result then is a system which impressively attains the object set by the inventor.

BRIEF DESCRIPTION OF THE DRAWINGS

Further advantages, features and details of the invention will be apparent from the following description of preferred embodiments and with reference to the drawing in which.

DETAILED DESCRIPTION

Figure 1:
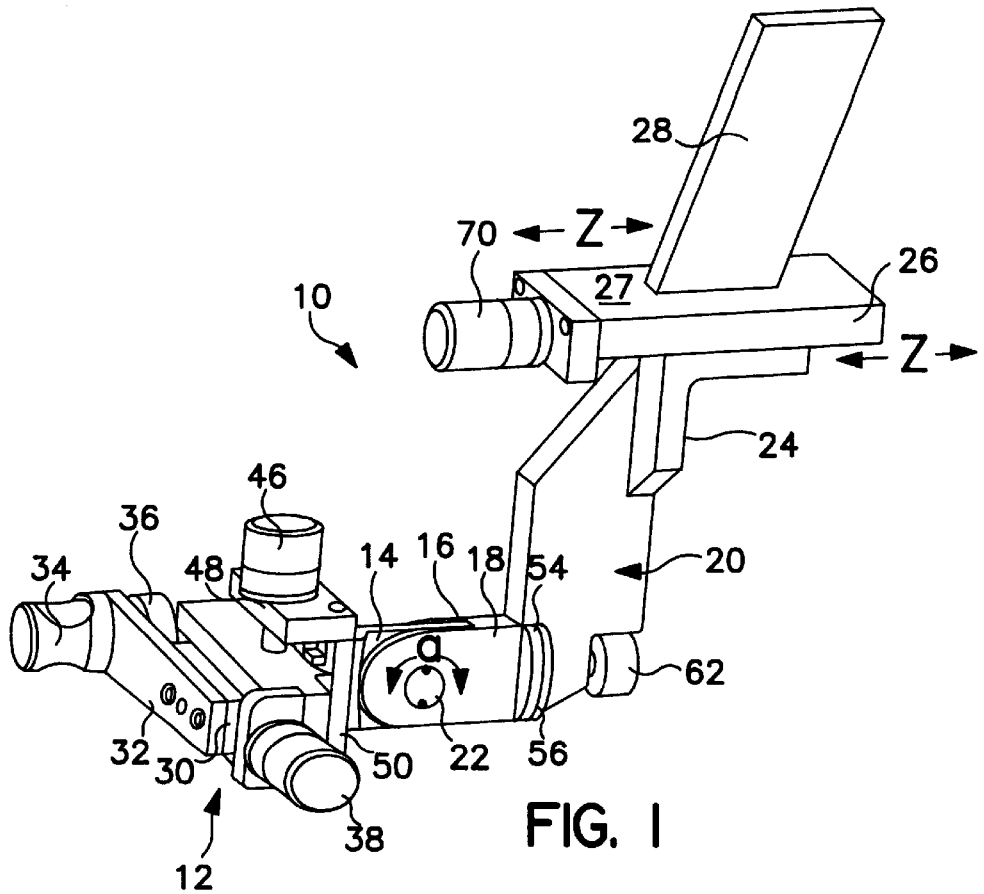
FIG. 1 shows a perspective view of a guide apparatus with working head for receiving an instrument.
Figure 2:
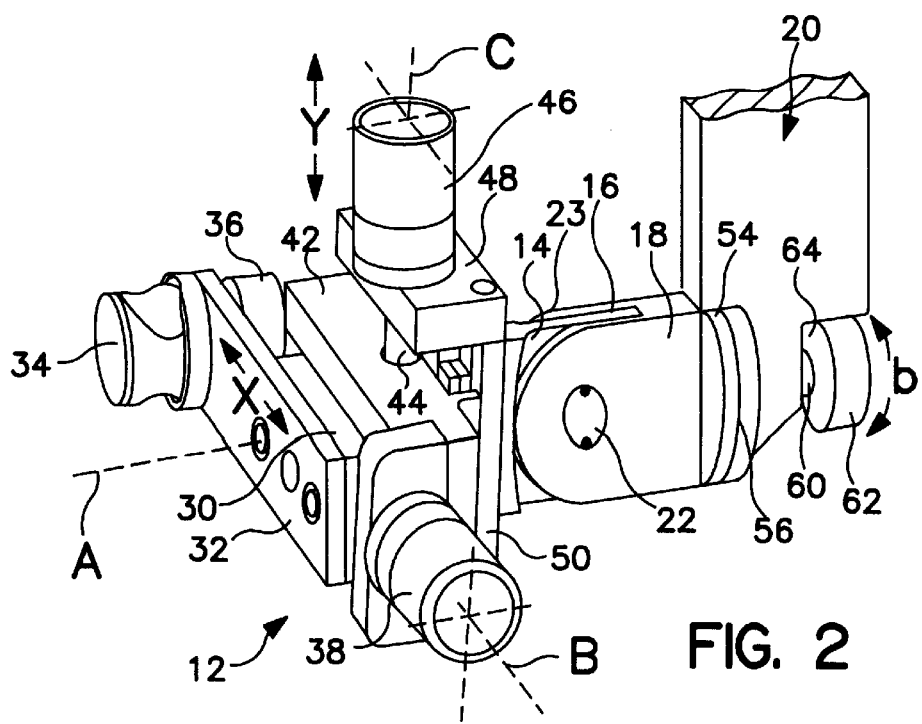
FIG. 2 is a perspective view on an enlarged scale of the working head having adjustable axes.
Figure 3:
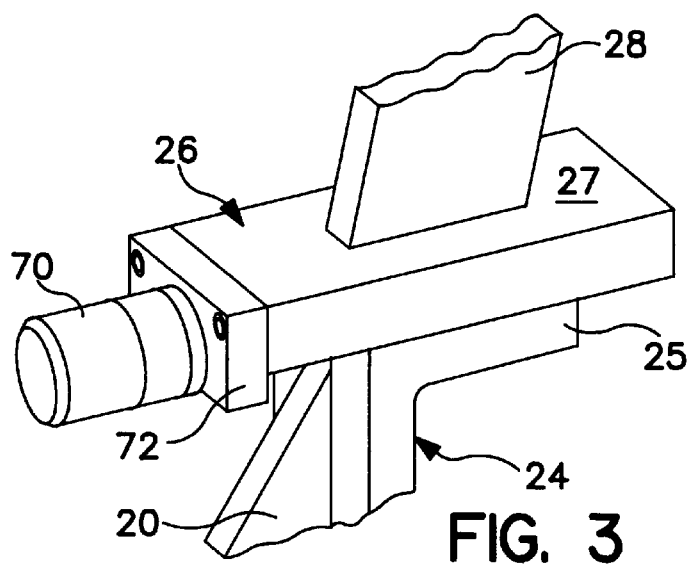
FIG. 3 is a perspective view of a displacement device for the working head.

A guide apparatus 10 for tools, in particular for medical instruments, has at the base thereof a working head 12 with a coupling arm 14 which projects in a bar-like manner; the latter is mounted in a receiving slot 16 in a forked carrier tongue 18 of an intermediate portion 20 and is rotatably connected to the carrier tongue 18 by a pivot pin 22; associated with the latter, at a free end, is a hand knob for initiating a rotational movement in the direction indicated by the arrow a.

Mounted at the upper end in FIG. 1 of the plate-like intermediate portion 20, on an angular base or support portion 24, is a flat rear carriage or slider 26, from the surface 27 of which a material strip 28 sticks up in a fin-like configuration. By means of that material strip 28 which serves as a holding portion, the guide apparatus 10 can be secured to a fixed point, for example a sturdy support stand, which is only indicated at F in FIG. 4 in the drawing for the sake of clarity thereof.

Provided on the working head 12 is a front carriage or slider 30 which is movable transversely with respect to the longitudinal axis A of the guide apparatus 10 and to which there is fixed a bar 32 which projects beyond it at one side; projecting from the bar 32 is a fixing ring or instrument holder 34 which is parallel to the longitudinal axis A, for receiving a drilling or milling head (not shown). The fixing ring 34 is provided with a securing knob 36 on the other side of the bar 32.

Figure 4:
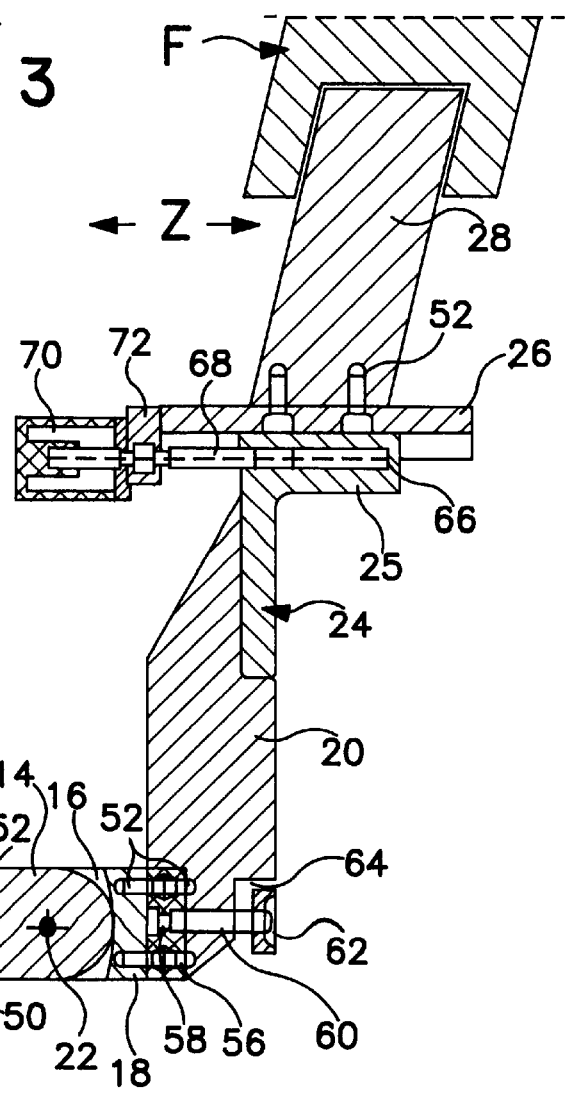
FIG. 4 is a view in longitudinal section through the guide apparatus taken along line IV—IV in FIG. 5.
Figure 5:
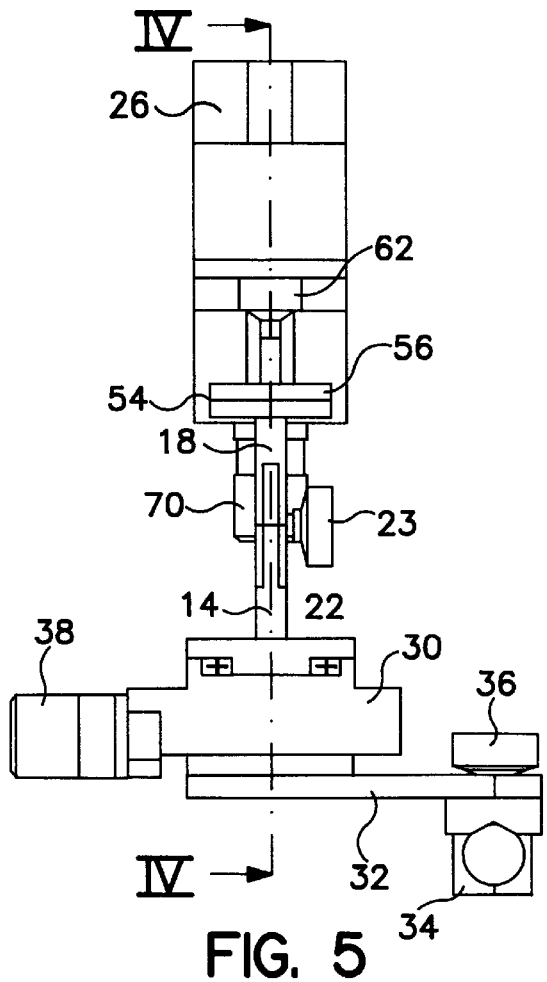
FIG. 5 is a view of the guide apparatus from below.
Figure 6:
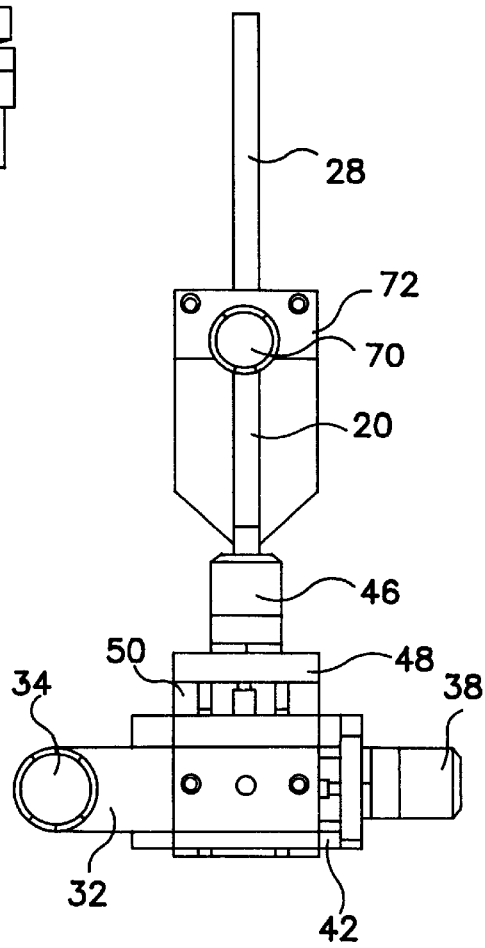
FIG. 6 is a front view of the guide apparatus.

The axis B of a laterally projecting rotary handle 38 extends parallel to the bar 32; the rotary handle 38 can be used to implement a horizontal movement—indicated by the arrow x—of the front carriage 30 for the fixing ring 34. FIG. 4 in particular shows that for that purpose the front carriage 30 is guided in a path or track which is afforded by a recess 40 in a rail 42 which is parallel to the bar 32 and which is horizontal in FIG. 4. The rail 42 is connected to a linkage 44, which is perpendicular thereto, of a further rotary handle 46 by means of which the rail 42—and therewith the front carriage 30—can be raised and lowered in the direction indicated by the arrow y; the axis of that linkage 44 is identified by C.

The rotary handle 46 is provided on a material strip 48 which in turn is carried on a vertical plate 50 which is disposed in front of the coupling arm 14 at the head end transversely with respect to the longitudinal axis A and which is screwed to the coupling arm 14. The carrier tongue 18 which receives the coupling arm 14 is fixedly connected at the other end by screws 52 to a rotary disk 54 which bears against a corresponding circular bearing surface of a bearing disk 56 at the base edge 58 of the plate-like intermediate portion 20.

The rotary disk 54 which is attached to a shaft 60 extending substantially on the longitudinal axis A is rotatable—in the direction indicated by the arrow b—through an angle of 360° about the longitudinal axis A and is to be fixed in its respectively selected position by means of a setting knob 62; the latter is disposed in a corner recess in the intermediate portion 20, as indicated at 64.

As already mentioned the intermediate portion 20 carries at its upper end the angular support portion 24 whose limb 25 which is disposed in terms of its cross-section in parallel relationship with the longitudinal axis A receives an adjusting spindle 68 in a passage 66. The spindle 68 is connected with its free end to a rotary handle 70 and upon actuation thereof produces a movement of the rear carriage 26 in the direction indicated by the arrow z. A front strip 72 of the rear carriage 26, through which the spindle 68 passes, serves as a support means for the rotary knob or handle 70.

Since, as mentioned, the fin-like material strip 28 which is fixedly connected to the rear carriage 26 is connected on the other hand as a holding fin member to a fixed point F, the rear carriage 26 or actuation of the rotary knob 70 thereof produces the forward and rearward movement—arrow z—of the working head 12 which is displaceable on the axes A, B, C and which is rotatable about the pivot pin 22 and the shaft 60 respectively.

After mounting a commercially available drilling or milling head to the working head 12, the described guide apparatus 10 serves for the production of recesses and bores in bone tissue in order to be able to fit implants with a high degree of precision. The working head 12 can be adjusted on a plurality of axes by the carriages 26, 30, 42 having a fine screwthread or the rotary pivots 22, 54/56, by hand or however electrically, electronically, pneumatically or hydraulically; replacement of the described setting knobs or rotary handles 38, 46, 70 which make it possible to move the carriages 30, 42, 26 by respective electrical, electronic, magnetic, pneumatic or hydraulic motors or drive means affords the possibility of automation which also makes it possible to control the guide apparatus 10 by way of a computer and in that way to produce the bores, slots and so forth with the desired degree of precision.

The corresponding drives are not illustrated in the drawing, nor are associated power cables or supply lines for flow media in that respect. The drawing also does not show sensors and measurement scales with which the exact measurement data can be set or recorded. For, displacement or movement of the individual axes A, B, C; 22, 54/56 by hand or by way of a drive unit can be monitored and if necessary corrected during a working operation by way of measurement scales (not shown) which are arranged at the individual regions of movement 26, 30, 42 and 22, 54/56 respectively and at which values transmitted by measurement sensors on a display screen or a measurement data display device appear during the operation.

In the case of a computer-controlled guide apparatus the movement program for the intervention by drilling and/or milling can be inputted beforehand so that the actual drilling and/or milling movement can be effected fully automatically.

I claim:

1. A guide apparatus comprising:

carriage fixed to a point (F);

an intermediate member having a first end received in said carriage and selectively movable in a first longitudinal co-ordinate direction z, and second end for pivotably receiving about a pivot axis (A) a coupling arm;

a working head secured to said coupling arm, said working head including an instrument holder, first means for moving said instrument holder in a second longitudinal co-ordinate direction x and a second means for moving said instrument holder in a third longitudinal co-ordinate direction y wherein said instrument holder is displaceable in three co-ordinate directions x, y, z and rotatable about pivot axis (A).

2. A guide apparatus as set forth in claim 2 characterized in that the instrument holder is mounted rotatably about the pivot axis (A) over an angle of more than 90°.

3. A guide apparatus as set forth in claim 1 characterized in that the instrument holder is arranged pivotably about a second pin which crosses the pivot axis (A).

4. A guide apparatus as set forth in claim 1 characterized in that the instrument holder is adapted to be displaceable in co-ordinate direction x transversely to a longitudinal axis (A) of the guide apparatus which is parallel to co-ordinate direction z on a front carriage the carriage includes means for lifting the front carriage and the instrument holder in co-ordinate direction y.

5. A guide apparatus as set forth in claim 1 characterized in that the instrument holder is mounted laterally of the working head on a bar which projects beyond same in a direction substantially perpendicular to axis (A).

6. A guide apparatus as set forth in claim 5 characterized in that a respective rotary handle is provided for the path of movement of the instrument holder transverse to longitudinal axis (A) and for lifting the carriage.

7. A guide apparatus as set forth in claim 1 characterized in that the working head is pivotably mounted by a pivot pin to a carrier tongue intermediate member.

8. A guide apparatus as set forth in claim 7 characterized in that the carrier tongue is arranged on intermediate member rotatably about a longitudinal axis (A) which is parallel to co-ordinate direction z.

9. A guide apparatus as set forth in claim 8 characterized in that the carrier tongue projects from a rotary disk which is fixed to a shaft and which is rotatably associated with a bearing surface of the intermediate member.

10. A guide apparatus as set forth in claim 9 characterized in that the rotary disk is connected by the shaft to a setting knob.

11. A guide apparatus as set forth in claim 1 characterized in that the path of movement of the carriage extends parallel to a longitudinal axis (A) of the guide apparatus which is parallel to co-ordinate direction z.

12. A guide apparatus as set forth in claim 1 characterized in that the carriage is connected to the intermediate member by an adjusting spindle and the adjusting spindle is provided with a rotary handle for actuation thereof.

13. A guide apparatus as set forth in claim 1 characterized in that the instrument holder is mounted rotatably about the pivot axis (A) over an angle of 360°.

* * * * *